United States Patent
Yan et al.

(10) Patent No.: US 10,123,740 B2
(45) Date of Patent: Nov. 13, 2018

(54) WEARABLE ACTION-AWARE DEVICE

(71) Applicant: Far Eastern New Century Corporation, Taipei (TW)

(72) Inventors: Min-Si Yan, Taoyuan (TW); Wei-Che Hung, Taoyuan (TW); Yueh-Hsien Lin, Taoyuan (TW); Chih-Ting Li, Taoyuan (TW)

(73) Assignee: Far Eastern New Century Corporation, Taipei (TW)

( * ) Notice: Subject to any disclaimer, the term of this patent is extended or adjusted under 35 U.S.C. 154(b) by 135 days.

(21) Appl. No.: 15/225,845

(22) Filed: Aug. 2, 2016

(65) Prior Publication Data

US 2017/0209093 A1 Jul. 27, 2017

(30) Foreign Application Priority Data

Jan. 22, 2016 (TW) .............................. 105102041 A

(51) Int. Cl.
*A61B 5/00* (2006.01)
*A41D 1/00* (2018.01)
(Continued)

(52) U.S. Cl.
CPC ............ *A61B 5/6804* (2013.01); *A41D 1/002* (2013.01); *A41D 31/00* (2013.01); *A61B 5/11* (2013.01);
(Continued)

(58) Field of Classification Search
CPC ......... A61B 5/6804; A61B 5/11; A61B 5/114; A61B 5/1116; A61B 5/1118;
(Continued)

(56) References Cited

U.S. PATENT DOCUMENTS 4,008,721 A    2/1977   Burton
4,580,572 A *  4/1986   Granek .............. A61B 5/04085
                                            600/388
(Continued)

FOREIGN PATENT DOCUMENTS

CN    102824176 B    6/2014
TW    201336474 A    9/2013
(Continued)

OTHER PUBLICATIONS

Gilsoo Cho et al., "Performance Evaluation of Textile-Based Electrodes and Motion Sensors for Smart Clothing", IEEE Sensors Journal., vol. 11, No. 12, Dec. 1, 2011, pp. 3183-3193.

*Primary Examiner* — Jameson Collier
(74) *Attorney, Agent, or Firm* — CKC & Partners Co., Ltd.

(57) ABSTRACT

The wearable action-aware device includes a clothing body, a signal receiving and computing element, and a conductive line made of conductive fabric. Two ends of the conductive line are electrically connected to the signal receiving and computing element, respectively, to form a circuit, and both the signal receiving and computing element and the conductive line are disposed on the clothing body. An exposed side of the conductive line has electrical conductivity, and the circuit is disposed on a part of the clothing body corresponding to a part of a body that needs to be measured. Action information of a user can be measured when the user wears the present invention wearable action-aware device.

10 Claims, 3 Drawing Sheets

(51) Int. Cl.
*A41D 31/00* (2006.01)
*A61B 5/11* (2006.01)
*A63B 24/00* (2006.01)
*G06F 1/16* (2006.01)
*H05K 1/03* (2006.01)
*H05K 1/09* (2006.01)

(52) U.S. Cl.
CPC ........ *A61B 5/1114* (2013.01); *A63B 24/0062* (2013.01); *G06F 1/163* (2013.01); *H05K 1/038* (2013.01); *H05K 1/092* (2013.01); *A61B 5/1116* (2013.01); *A61B 5/1118* (2013.01); *A61B 5/1121* (2013.01); *H05K 2201/0145* (2013.01); *H05K 2201/0162* (2013.01)

(58) Field of Classification Search
CPC ... A61B 5/1121; A41D 1/002; A63B 24/0062; H05K 1/038; H05K 1/092; H05K 2201/0145; H05K 2201/0162
See application file for complete search history.

(56) References Cited

U.S. PATENT DOCUMENTS

| | | | | |
|---|---|---|---|---|
| 5,211,174 | A * | 5/1993 | Imran | A61B 5/0408 252/500 |
| 5,652,955 | A * | 8/1997 | Skewis | A41D 13/088 2/16 |
| 6,047,203 | A * | 4/2000 | Sackner | A41D 13/1281 600/301 |
| 7,502,643 | B2 * | 3/2009 | Farringdon | A61B 5/0428 600/509 |
| 8,123,622 | B1 | 2/2012 | Young et al. | |
| 8,416,102 | B2 * | 4/2013 | Yin | A61B 5/1118 341/20 |
| 8,948,839 | B1 * | 2/2015 | Longinotti-Buitoni | A61B 5/6804 29/825 |
| 2005/0054941 | A1 * | 3/2005 | Ting | A61B 5/0408 600/529 |
| 2007/0032719 | A1 * | 2/2007 | Menon | C09J 133/06 600/391 |
| 2007/0148399 | A1 * | 6/2007 | Chen | B32B 33/00 428/96 |
| 2009/0229039 | A1 * | 9/2009 | Kuck | A41D 13/1254 2/338 |
| 2010/0063779 | A1 * | 3/2010 | Schrock | A43B 3/00 702/188 |
| 2011/0166491 | A1 * | 7/2011 | Sankai | A41D 13/1281 601/84 |
| 2013/0066168 | A1 * | 3/2013 | Yang | A61B 5/0245 600/301 |
| 2013/0137943 | A1 * | 5/2013 | Pinto Rodrigues | A61B 5/01 600/301 |
| 2013/0317648 | A1 * | 11/2013 | Assad | B25J 9/1694 700/258 |
| 2014/0070957 | A1 * | 3/2014 | Longinotti-Buitoni | A61B 5/02055 340/870.01 |
| 2014/0135593 | A1 * | 5/2014 | Jayalth | A61B 5/0022 600/301 |
| 2014/0135608 | A1 * | 5/2014 | Gazzoni | A61N 1/04 600/395 |
| 2014/0318699 | A1 * | 10/2014 | Longinotti-Buitoni | A61B 5/0002 156/247 |
| 2015/0019135 | A1 | 1/2015 | Kacyvenski et al. | |
| 2015/0045699 | A1 * | 2/2015 | Mokaya | A61B 5/0024 600/595 |
| 2015/0143601 | A1 | 5/2015 | Longinotti-Buitoni | |
| 2015/0148619 | A1 * | 5/2015 | Berg | A61B 5/0024 600/301 |
| 2015/0257711 | A1 * | 9/2015 | Chen | A61B 5/7282 601/134 |
| 2015/0366504 | A1 | 12/2015 | Connor | |
| 2016/0000374 | A1 | 1/2016 | Dandekar et al. | |
| 2016/0157779 | A1 * | 6/2016 | Baxi | A61B 5/6831 600/301 |
| 2017/0075481 | A1 * | 3/2017 | Chou | G06F 3/044 |
| 2017/0259428 | A1 * | 9/2017 | Assad | B25J 9/163 |

FOREIGN PATENT DOCUMENTS

| | | |
|---|---|---|
| TW | 201509486 A | 3/2015 |
| TW | 201515636 A | 5/2015 |
| TW | M511299 U | 11/2015 |
| WO | 2012054231 A2 | 4/2012 |

* cited by examiner

1

WEARABLE ACTION-AWARE DEVICE

RELATED APPLICATIONS

This application claims priority to Taiwanese Application Serial Number 105102041, filed Jan. 22, 2016, which is herein incorporated by reference.

BACKGROUND

Field of Invention

The present invention relates to an action-aware device. More particularly, the present invention relates to a wearable action-aware device integrated with fabric. Users are able to obtain their action information, such as an exercise action state of the users, by reassuring through wearing the present invention wearable action-aware device.

Description of Related Art

With the progress of social economy, science and technology, and living standards, people have already developed more profound realization of the importance of health. In addition to putting emphasis on a health diet, exercise is emphasized even more to maintain good health.

However, an exerciser usually does not understand the action information during exercise, such as whether the action is correct. In order to understand the action information during exercise, an action-aware device is necessary. A prior art sensing device (or called a sensor) detects external information by employing natural physical or biological characteristics, and the sensing device has continued developing with the progress of science and technology. In combination with knowledge accumulated by people in the fields of science, physics, and medicine, nowadays not only has the sensor been used as a tool for exploring knowledge by people, but the sensor can also provide lives with more convenient services when combined with communication, Internet of Things, and computation of big data in the cloud.

In the prior art action measurement, an action-aware device can be utilized to measure actions of a human body, which is performed by directly placing plural sensors on the human body. Generally speaking, the method of sensing "actions" of a human body comprises detecting direction and speed (acceleration sensor), and the like. Hence, the prior art action sensing method usually requires measuring changes of physical quantities (gravity, speed), so that a structure constituted by mechanical components is normally adopted. However, today's micro-electromechanical systems (MEMS) have become an advanced process technology that can miniaturize a traditional mechanical system to the size of a chip. Nowadays, the MEMs also have become an important technology through which the action sensors can be placed into many wearable devices, such as mobile phones, watches, etc.

As mentioned above, the acceleration sensor, which is also called a gravity sensor (G-Sensor) or an accelerometer, performs measurements by detecting movement and speed of a human body. If directions are also added, one acceleration sensor can sense an axial direction, two acceleration sensors can sense plane shifts (X, Y), and three acceleration sensors that are referred to as a triaxial acceleration sensor can perform a full range of three-dimensional sensing (X, Y, Z). Acceleration sensors have already been applied to the somatosensory control. For example, the actions of a hand can be detected by just waving the wii remote in the hand in the control method of game consoles wii. Such kind of wearable devices can also be used for measuring walking steps, distance, computing calories that have been consumed, etc. when been applied to exercise.

In addition, it has been proposed that the electromyography (EMG) is used to analyze human actions. The EMG is a physiological sensor of electrical characteristics of muscle. By sensing the action potential generated because of muscular contraction or relaxation, the human actions are detected.

The prior arts mentioned above all have a certain effect on understanding the human exercise state. However, plural sensors need to be respectively placed on limbs when the human action is measured to measure the actions of the limbs. Not only do the sensors placed on limbs increase the burden of the user, but they also increase the cost of the measurement device. Additionally, the signal quality is not stable, such as too many noises, weak signals, etc.

For the forgoing reasons, there is a need to provide an action sensing technology that imposes no burden on users and has a lower cost.

SUMMARY

It is an objective of the present invention to provide a wearable action-aware device to measure action information of a user.

A wearable action-aware device is provided. The wearable action-aware device comprises a clothing body, a signal receiving and computing element, and a conductive line made of conductive fabric. Two ends of the conductive line are electrically connected to the signal receiving and computing element, respectively, to form a circuit, and both the signal receiving and computing element and the conductive line are disposed on the clothing body. An exposed side of the conductive line has electrical conductivity, and the circuit is disposed on a part of the clothing body corresponding to a part of a body that needs to be measured.

In one or more embodiments, the present invention wearable action-aware device at least drapes over one joint of a user when being worn by the user, and the circuit is disposed on a part of the clothing body corresponding to the joint.

In one or more embodiments, the conductive line preferably has a line resistance value not more than $1 \times 10^6$ ohms.

The present invention wearable action-aware device can be fabricated in a form of clothing so that a user can wear the present invention wearable action-aware device just like a general piece of clothing without any extra burden. In one of more embodiments, when the user wearing the present invention wearable action-aware device exercises, the circuit bends because the joint bends so as to change the current amount under the same voltage. In one or more embodiments, the user contacts one portion of the conductive line with another portion of the conductive line of the wearable action-award device to change a path of the circuit. In this manner, the frequency and the extent of the current change can thus be used to measure the action information of the user.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings

DESCRIPTION OF THE EMBODIMENTS

Figure 1:
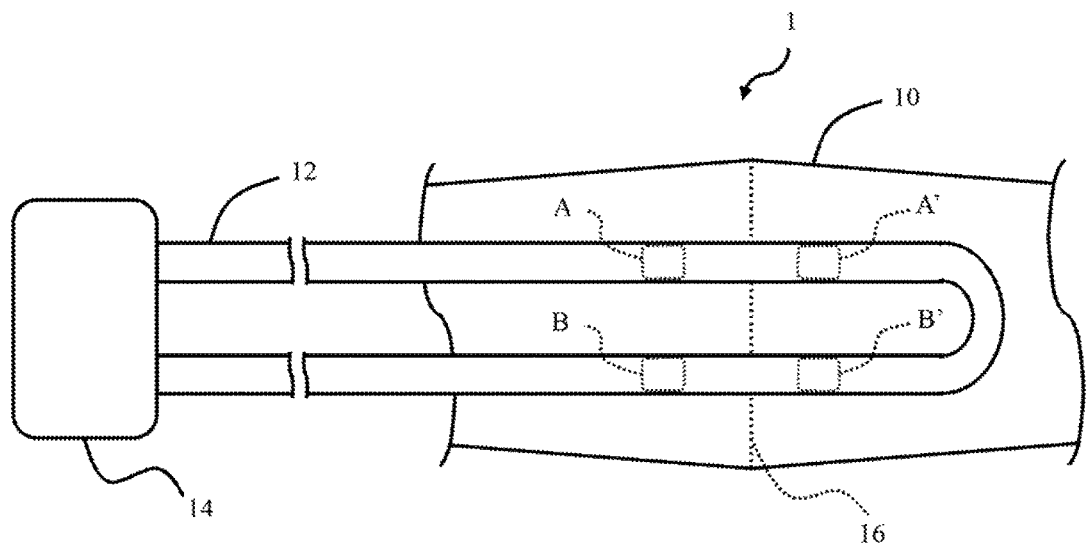
FIG. 1 depicts a local schematic diagram of a wearable action-aware device according to one embodiment of this invention.

Reference will now be made in detail to the present embodiments of the invention, examples of which are illustrated in the accompanying drawings. Wherever possible, the same reference numbers are used in the drawings and the description to refer to the same or like parts.

A description is provided with reference to FIG. 1. FIG. 1 depicts a local schematic diagram of a wearable action-aware device according to one embodiment of this invention. A wearable action-aware device according to the present invention mainly comprises a clothing body 10, a signal receiving and computing element 14, and a conductive line 12. The conductive line 12 is made of conductive fabric, and two ends of the conductive line 12 are electrically connected to the signal receiving and computing element 14, respectively, to form a circuit. The signal receiving and computing element 14 and the conductive line 12 are both disposed on the clothing body 10, and an exposed side of the conductive line 12 (that is, the side opposite to a side where the conductive line 12 is joined with the clothing body 10) has electrical conductivity (that is, an electrical connection to any conductive object can be formed by contacting the conductive object) so as to constitute a wearable action-aware device 1 according to the present invention.

In one or more embodiments, when a user wears the present invention wearable action-aware device 1, the present invention wearable action-aware device 1 is preferably draped over at least one joint of the user, and the above circuit is disposed on a part of the clothing body 10 corresponding to the joint.

In one or more embodiments, the conductive line preferably has a line resistance value not more than $1\times10^6$ ohms, more preferably from 1 to $1\times10^5$ ohms, most preferably from 10 to $1\times10^4$ ohms.

In one or more embodiments, the conductive line preferably has a width not less than 0.5 centimeters (cms), more preferably from 0.8 to 5 centimeters (cms).

As long as the clothing body 10 can be used as the fabric or nonwoven fabric worn by the user, it can be applied to the present invention. The present invention is not limited in this regard. The above nonwoven fabric may be, for example, clothing made of a natural or synthetic resin film, but the present invention is not limited in this regard. The above fabric comprises non-woven fabric, knit fabric, or weaving fabric. In one or more embodiments, the clothing body 10 has stretchability. The stretchability can be obtained by designing a material or a structure of the fabric or the nonwoven fabric, for example, designing a texture structure of knit fabric, or further adding elastic yarns (such as LYCRA® elastic yarns) to the knit fabric or weaving fabric, but the present invention is not limited in this regard.

The signal receiving and computing element 14 is mainly used for providing the circuit with a stable voltage source. In addition to that, the signal receiving and computing element 14 is further used for receiving current change information from the conductive line 12 and performing a conversion operation on the current change information to obtain needed action information of the user. The signal receiving and computing element 14 can further be integrated with a wireless signal transmit unit so that electrical signals can be transmitted. The wireless signal transmit unit can also be disposed by itself separate from the signal receiving and computing element 14, and is electrically connected to the signal receiving and computing element 14.

Figure 2:
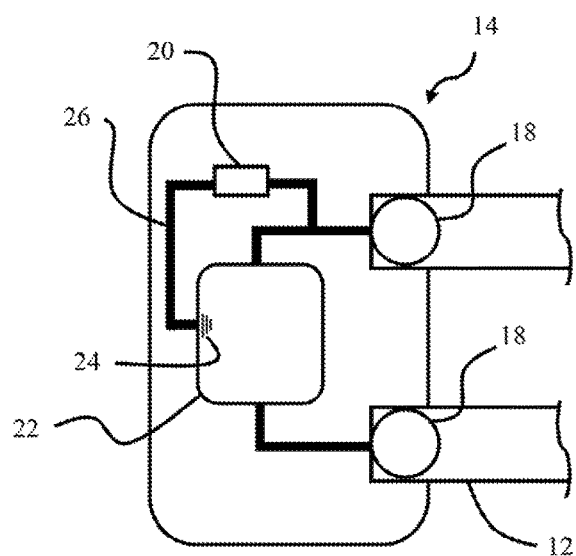
FIG. 2 depicts a schematic diagram of a signal receiving and computing element in a wearable action-aware device according to this invention.

A description is provided with reference to FIG. 2. FIG. 2 depicts a schematic diagram of the signal receiving and computing element 14 in the wearable action-aware device 1 according to this invention. Two terminals of the conductive line 12 are electrically connected to a current signal output terminal and an input terminal of the signal receiving and computing element 14, respectively, through electrical contacts 18 so as to constitute a complete circuit. The signal receiving and computing element 14 at least comprises a signal conversion operation unit 22 and a power supply element (not shown in the figure). The power supply element can continuously output a stable voltage passing the circuit. Any prior art power supply element that can achieve such an objective can be applied to the present invention, and the present invention is not limited in this regard. For example, a battery can be used, but the present invention is not limited to this.

When the present invention wearable action-aware device 1 operates, the power supply element in the signal receiving and computing element 14 outputs a current caused by a stable voltage to pass the electrical contact 18, pass the conductive line 12, and then return to the signal receiving and computing element 14 via the electrical contact 18 at the other end of the conductive line 12, thus forming a complete circuit.

In order to adjust the sensitivity of the current change information received by the signal conversion operation unit 22, a resistor 20 can be further connected in series with a line 26 between the electrical contact 18 and the signal conversion operation unit 22 and the line 26 passing the resistor 20 is connected to a ground terminal (GND) 24 of the signal conversion operation unit 22. The resistor 20 may be selected depending on the required detection sensitivity, and the present invention is not limited in this regard. In one or more embodiments, the resistor 20 is an adjustable resistance element, such as a rheostat, but the present invention is not limited in this regard.

Figure 3:
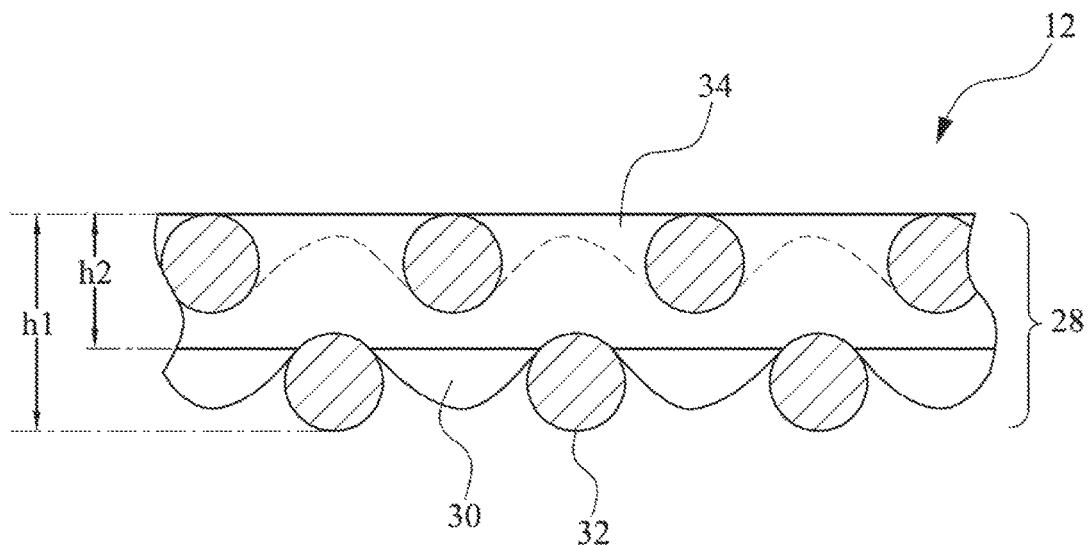
FIG. 3 depicts a cross-sectional schematic diagram of a conductive line according to one embodiment of this invention.

In one or more embodiments, the conductive line 12 is preferably made of conductive fabric. More preferably, the conductive fabric is constituted by a fabric body 28 and a conductive coating layer 34 embedded in the fabric body 28. A description is provided with reference to FIG. 3. In the present embodiment, the fabric body 28 is weaving fabric, which is obtained by interweaving a plurality of warp yarns 30 and a plurality of weft yarns 32. In this manner, the fabric body 28 has a thickness h1 formed by interweaving yarns. The conductive coating layer 34 is embedded in the fabric body 28 from one side of the fabric body 28, and is filled into voids between the interwoven yarns of the fabric body 28 and integrated into one.

According to the present embodiment, the conductive coating layer 34 is completely merged with the fabric body 28 and is embedded in the fabric body 28. An upper side of the conductive coating layer 34 is substantially aligned with an upper side of the fabric body 28. A lower side of the conductive coating layer 34 is located in the fabric body 28. In this manner, an appearance that the conductive coating layer 34 is substantially leveled with the upper side of the fabric body 28 is presented. In examples, one side of the conductive coating layer 34 is flush with a side of the fabric body 28. In the embodiment, a thickness h2 of the conductive coating layer 34 is not more than the thickness h1 of the fabric body 28.

Figure 4:
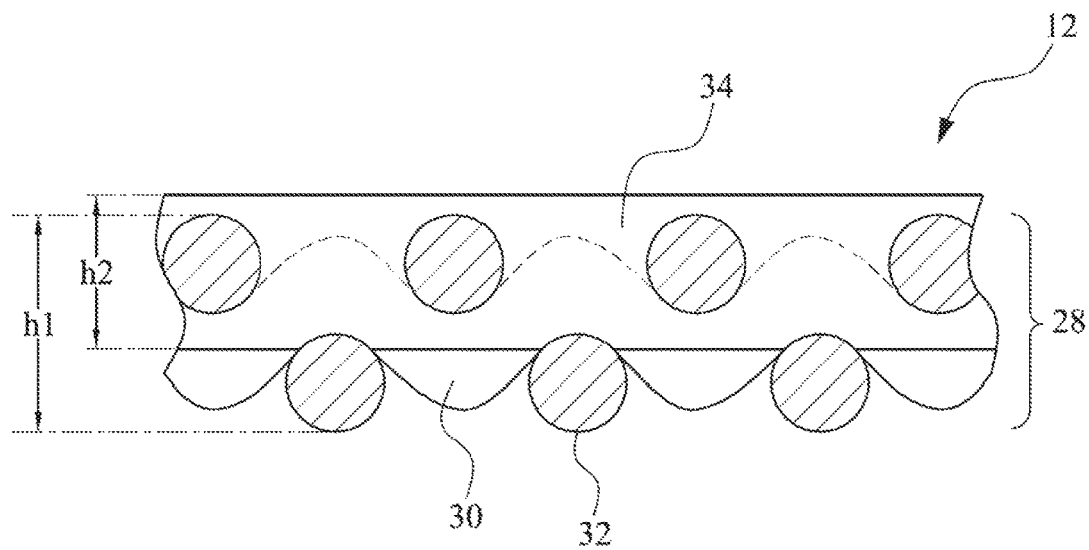
FIG. 4 depicts a cross-sectional schematic diagram of a conductive line according to another embodiment of this invention.

A description is provided with reference to FIG. 4. FIG. 4 depicts a cross-sectional schematic diagram of a conductive line according to another embodiment of this invention. According to the present embodiment, conductive fabric is also basically constituted by the fabric body 28 and the conductive coating layer 34 embedded in the fabric body 28. The difference is that the conductive coating layer 34 is partially embedded in the fabric body 28. That is, part of a thickness of the conductive coating layer 34 projects out of the fabric body 28.

The thickness of the conductive coating layer 34 that projects out of the fabric body 28 is not limited according to the present invention. In one or more embodiments, the thickness is preferably not more than 40 micrometers (μm), more preferably not more than 30 μm, and most preferably not more than 20 μm.

In the previous embodiments, although only the fabric body 28 that is weaving fabric is taken as an example for illustration, those of ordinary skill in the art would understand that knit fabric can also be used as the fabric body 28 based on the description of the present invention.

Since the conductive coating layer 34 is completely embedded in the fabric body 28 or most of the conductive coating layer 34 is embedded in the fabric body 28 according to the present invention conductive line 12, the fabric body 28 will further provides the conductive coating layer 34 with physical support and protection. Structural strength of the conductive coating layer 34 is therefore enhanced. In this manner, the conductive line 12 has the structural strengthening effect similar to that owned by a composite material but at the same time retains the softness close to that of general fabric, thus providing users with better wearing comfort. In one or more embodiments, a thickness of the conductive coating layer 34 embedded in the fabric body 28 is preferably from 10 to 50 μm, more preferably from 20 to 40 μm. If the thickness is less than 10 μm, the conductive coating layer 34 peels from a surface of the fabric body 28 easily. On the contrary, if the thickness is more than 50 μm, the resistance value tends to be not uniform to affect the measurement result of current change.

The conductive coating layer 34 is constituted by a hydrophobic adhesive and a plurality of conductive particles dispersed in the hydrophobic adhesive. The plurality of conductive particles in the conductive coating layer is from 20 to 70 wt %. A material that can be applied to the present invention to serve as a material of the hydrophobic adhesive comprises, but is not limited to, polyurethane (PU), siloxane resin, polyethylene terephthalate (PET), or polyacrylate, etc. A material that can be applied to the present invention to serve as a material of the conductive particles comprises a non-metallic material, a metallic material, or combinations thereof. The non-metallic material comprises, but is not limited to, a carbon nanotube (CNT), carbon black, carbon fiber, graphene, or a conductive polymer (such as poly (3,4-ethylenedioxythiophene (PEDOT), polyacrylonitrile (PAN), etc.), and the like. CNT is the most preferable one. The metallic material comprises, but is not limited to, gold, silver, copper, or a metal oxide (such as indium tin oxide (ITO)), etc.

The conductive coating layer 34 can be embedded in the fabric body 28 by using any prior art method. For example, the hydrophobic adhesive is dissolved in a solvent, and the conductive particles are dispersed therein to form conductive coating liquid. After that, the conductive coating liquid is coated on the fabric body 28 and penetrates into the fabric body 28 to form a conductive coating layer. Finally, the conductive coating layer is baked and completely dried, but the present invention is not limited in this regard.

Those of ordinary skill in the art would understand that the above conductive fabric may also be, for example, conductive fabric woven with conductive yarns through the above description of the present invention, and the present invention is not limited in this regard.

When the conductive line 12 is disposed on the clothing body 10, one side of the conductive line 12 that does not have electrical conductivity is joined with the clothing body 10 so that the conductive coating layer 34 is exposed. The joining method is not limited according to the present invention. Any prior art method that can be used to place the conductive line 12 on the clothing body 10 may be applied to the present invention, which comprises, but is not limited to, bonding by using an adhesive or stitching.

Figure 5:
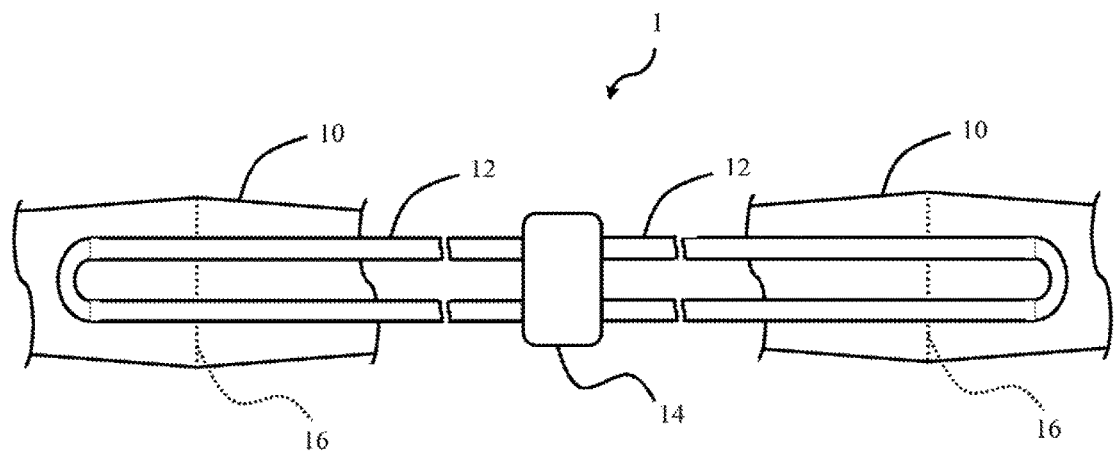
FIG. 5 depicts a local schematic diagram of a wearable action-aware device according to another embodiment of this invention.

A description is provided with reference to FIG. 5. FIG. 5 depicts a local schematic diagram of the wearable action-aware device 1 according to another embodiment of this invention. The present invention wearable action-aware device 1 comprises the two conductive lines 12 electrically connected to the signal receiving and computing element 14 to form two circuits according to the present embodiment. In this manner, the signal receiving and computing element 14 can simultaneously receive action information from two different sensing parts of a user's body. The above description is only taken as an example. Those of ordinary skill in the art may simultaneously connect three or more than three circuits by using the same method through the disclosure of the present invention.

Figure 6:
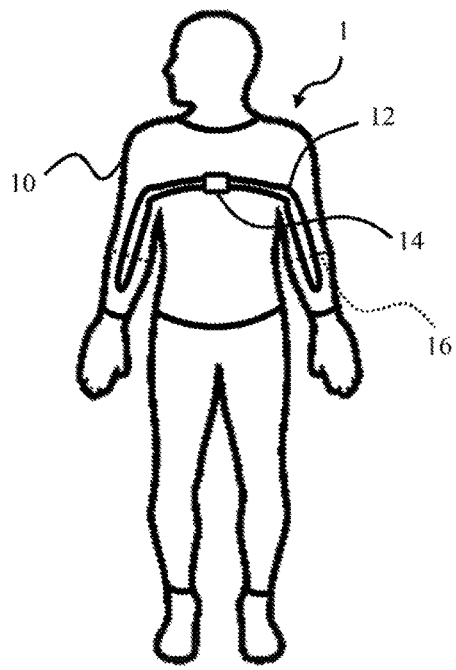
FIG. 6 depicts a schematic diagram of a wearable action-aware device when being worn by a user according to this invention.

A description is provided with reference to FIG. 6. FIG. 6 depicts a schematic diagram of the wearable action-aware device 1 when being worn by a user according to this invention. The conductive line 12 in the wearable action-aware device 1 is disposed on the clothing body 10 corresponding to a user's arms, and a circuit thus formed passes joint bending lines 16. With additional reference to FIG. 1, when the user wearing the present invention wearable action-aware device 1 exercises to bend elbows, the clothing body 10 at bends of the elbows will be squeezed and wrinkled, so that a contact point A touches a contact point A' and a contact point B touches a contact point B' in the conductive line 12. Hence, a current will bypass the conductive line 12 between the contact point A and the contact point A' and the conductive line 12 between the contact point B and the contact point B' to shorten a path of the conductive line 12 through which the current actually flows. Thus, a total resistance of the circuit is reduced to increase the current so as to generate current change information. The current change information comprises changes of intensity and frequency. After the current change information is received by the signal receiving and computing element 14, the signal receiving and computing element 14 further converts the current change information into user's action information. Finally, the users action information is transmitted to a receiving device by a wireless signal transmission method, for example, a variety of prior art smart portable devices, such as a smart phone, a watch, a bracelet, or a tablet personal computer, etc.

In one or more embodiments, when the user wearing the present invention wearable action-aware device 1 exercises, the circuit of the conductive line 12 can be disposed depending on a position at which the action needs to be measured, as long as different parts of the conductive line 12 can touch each other when the user acts to change the path of the conductive line 12 through which the current actually flows and generate the current change information.

Embodiment

Polyurethane (commercially available product, Model CD-5030) is dissolved in n-Butyl acetate (nBAC) to prepare polyurethane coating liquid (solid content 30 wt %). Then, nanotubes (commercially available product, double-walled carbon nanotubes) are added into the polyurethane coating liquid. The weight ratio is 1:5 (nanotubes: polyurethane coating liquid). Uniformly mix the nanotubes with the polyurethane coating liquid to obtain conductive coating liquid. The conductive coating liquid is printed on weaving fabric (commercially available product, 30 Denier weaving fabric) through the screen printing technology by using a 200 mesh screen (commercially available product, Model PET) and is then dried by using hot air at a temperature of 150° C. to remove solvent so as to form a conductive coating layer embedded in the weaving fabric. The present invention conductive line (a thickness of the conductive coating layer is 40 μm in which a thickness embedded in the weaving fabric is 10 μm) can thus be fabricated. Under the circumstances, a percentage occupied by the nanotubes in the conductive coating layer is 40 wt %.

Take one piece of clothing to serve as a clothing body. A signal receiving and computing element is disposed on a chest portion or a back portion of the clothing. The conductive line is cut to have a width of 1 cm and is electrically connected to the signal receiving and computing element and laid along arm portions of the clothing body. Finally, the conductive line returns to the signal receiving and computing element and is electrically connected to the signal receiving and computing element to form a circuit.

Turn on the power of the signal receiving and computing element to continuously supply the circuit with a stable voltage of 3 volts. When a user wearing the present invention wearable action-aware device bends an elbow, the signal receiving and computing element will receive current change information so as to obtain information on whether the user's action is accurate and times of actions. At the same time, a frequency of current change can be used to calculate an action frequency and an action speed. Other exercise action information, comprising information such as calorie consumption state, etc., of the user can be further calculated by using prior art software, but the present invention is not limited in this regard.

The information measured by the present invention wearable action-aware device can be further combined with the information measure by a physiological sensing device. More information, such as running posture, muscle fatigue, exercise intensity, etc., can be obtained by using software to perform calculation.

In summary, the present invention has utility and inventive step, and the present invention also has novelty because the present invention is not disclosed in any publication, thus fulfilling the requirements of patentability of inventions specified in Article 102 and Article 103 of the Patent Act.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A wearable action-aware device comprising:
a clothing body used for draping over at least one joint of a user when being worn by the user;
a signal receiving and computing element; and
a conductive line made of conductive fabric, two ends of the conductive line being electrically connected to the signal receiving and computing element, respectively, to form a circuit, and both the signal receiving and computing element and the conductive line being disposed on the clothing body, wherein the conductive fabric comprises a fabric body and a conductive coating layer, and the conductive coating layer comprises a hydrophobic adhesive and a plurality of conductive particles dispersed in the hydrophobic adhesive, wherein the conductive coating layer is completely merged with the fabric body and embedded in the fabric body, and the conductive coating layer has an exposed surface that is flush with a side of the fabric body, wherein an exposed side of the conductive line has electrical conductivity, and the circuit is disposed on a part of the clothing body corresponding to the at least one joint.

2. The wearable action-aware device of claim 1, wherein a width of the conductive line is not less than 0.5 centimeter.

3. The wearable action-aware device of claim 2, wherein the width of the conductive line is from 0.8 to 5 centimeters.

4. The wearable action-aware device of claim 1, wherein a line resistance value of the conductive line is not more than $1 \times 10^6$ ohms.

5. The wearable action-aware device of claim 4, wherein the line resistance value of the conductive line is from 1 to $1 \times 10^5$ ohms.

6. The wearable action-aware device of claim 1, wherein the conductive coating layer is embedded in the fabric body from one side of the fabric body and has a flat surface, and a thickness of the conductive coating layer is not more than a thickness of the fabric body.

7. The wearable action-aware device of claim 6, wherein the fabric body is weaving fabric.

8. The wearable action-aware device of claim 6, wherein the hydrophobic adhesive is selected from the group consisting of polyurethane, polysiloxane, polyethylene terephthalate, polyacrylate and a combination thereof.

9. The wearable action-aware device of claim 6, wherein the plurality of conductive particles are metallic conductive particles or non-metallic conductive particles.

10. The wearable action-aware device of claim 6, wherein the plurality of conductive particles in the conductive coating layer is from 20 to 70 wt %.

\* \* \* \* \*